United States Patent [19]

Bluthé et al.

[11] Patent Number: 4,510,330

[45] Date of Patent: Apr. 9, 1985

[54] PROCESS FOR THE PREPARATION OF δ-ETHYLENIC CARBONYL COMPOUNDS

[75] Inventors: Norbert Bluthé, Villeurbanne; Jacques Goré, Caluire; Max Malacria, Villeurbanne, all of France

[73] Assignee: Rhone-Poulenc Sante, Courbevoie, France

[21] Appl. No.: 390,700

[22] Filed: Jun. 21, 1982

[30] Foreign Application Priority Data

Jun. 23, 1981 [FR] France .................................. 81 12301

[51] Int. Cl.³ .............................................. C07C 45/51
[52] U.S. Cl. ...................................... 568/403; 568/361
[58] Field of Search ......................... 568/361, 403, 404

[56] References Cited

PUBLICATIONS

Overman et al., Tet. Letters, vol. 24, pp. 2235–2238 and 3757–3760, (1983).
Ryu et al., Tet. Letters, vol. 21, pp. 4283–4286, (1980).
Theissen, J. Org. Chem., vol. 36, pp. 752–757, (1971).
Shimizu et al., Tet. Letters, vol. 24, pp. 1797–1800, (1983).
Hamilton, J. Chem. Soc., Chem. Comm., pp. 456–457, (1981).
Overman et al., J.A.C.S., vol. 102, #2, pp. 865–867, (1980).
"Organic Reactions", vol. 22, John Wiley & Sons, pp. 51 to 65, (1976).

*Primary Examiner*—James H. Reamer
*Attorney, Agent, or Firm*—Stevens, Davis, Miller & Mosher

[57] ABSTRACT

Process for the preparation of δ-ethylenic carbonyl compounds of the formula:

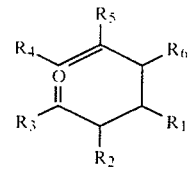

by the oxy-Cope rearrangement of a diethylenic alcohol of the formula:

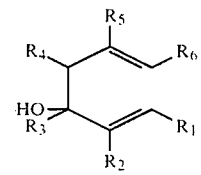

in which the transformation is carried out in the presence of a catalytic amount of a divalent palladium compound.

In the depicted formulae $R_1$, $R_4$ and $R_6$ each represent a hydrogen atom or a hydrocarbon radical, $R_2$ represents a hydrogen atom and $R_3$ and $R_5$ each represent a hydrocarbon radical, or $R_3$ and $R_4$ together represent an alkylene radical ($-CH_2-$)$_n$ (wherein n is an integer from 3 to 20 inclusive) in which one or more carbon atoms can optionally carry as substituent(s) one or more alkyl radicals containing 1 to 4 carbon atoms.

The carbonyl products are useful as starting materials for the preparation of compounds intended for use in pharmacy, in agriculture or perfumery.

8 Claims, No Drawings

PROCESS FOR THE PREPARATION OF δ-ETHYLENIC CARBONYL COMPOUNDS

DESCRIPTION

The present invention relates to a process for the preparation of δ-ethylenic carbonyl compounds of the general formula:

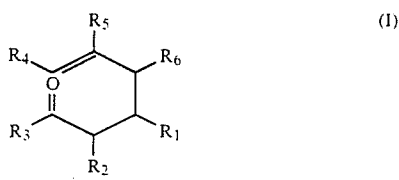

wherein $R_1$, $R_4$ and $R_6$, which may have the same or different significances, each represent a hydrogen atom or a hydrocarbon radical, $R_2$ represents a hydrogen atom and $R_3$ and $R_5$, which may have the same or different significances, each represent a hydrocarbon radical, or $R_3$ and $R_4$ together represent an alkylene radical $(-CH_2-)_n$ (wherein n represents an integer from 3 to 20 inclusive) in which one or more carbon atoms can optionally carry as substituent(s) one or more alkyl radicals containing 1 to 4 carbon atoms (preferably methyl), by the rearrangement of a diethylenic alcohol of the general formula:

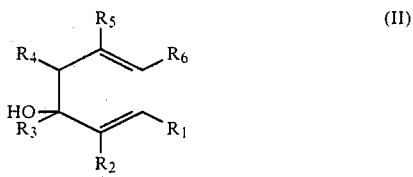

wherein $R_1$, $R_2$, $R_3$, $R_5$ and $R_6$ are as hereinbefore defined.

By the term "hydrocarbon radical" is meant an acyclic radical containing 1 to 20 carbon atoms, the chain of which can contain one or more double or triple bonds, e.g. an alkyl radical containing 1 to 20 carbon atoms, or an alkenyl or alkynyl radical containing 2 to 20 carbon atoms, such unsaturated radicals optionally having several double or triple bonds present. Preferred acyclic radicals are alkyl radicals containing 1 to 10 carbon atoms or alkenyl radicals containing 2 to 10 carbon atoms with at most three (preferably two) double bonds therein and optionally carrying on one or more of the carbon atoms a methyl substituent. Preferably $R_1$ and $R_6$ represent hydrogen atoms, and preferably $R_5$ represents the methyl radical.

The carbonyl compounds of general formula (I) are particularly valuable intermediates for the preparation of products having biological activity. More particularly, the compounds of general formula (I) can be applied in the synthesis of products intended for pharmacy (vitamins A and E), agrochemistry or perfumery.

The rearrangement of a diethylenic alcohol of general formula (II) to a carbonyl product of general formula (I) is a known reaction generally referred to as an oxy-Cope rearrangement. The oxy-Cope rearrangement has formed the subject of a number of studies, but, on account of the conditions used for carrying it out, its practical interest has been very limited.

For example, vapour-phase thermolysis according to the process described by A. Viola et al., J. Amer. Chem. Soc., 89, 3462 (1967), is of low stereoselectivity and leads to by-products from degradation and polymerisation, the origin of which is due to the high temperatures (of the order of 300° C.) required for the rearrangement.

It has been shown, in particular by Y. Fujita et al., Chem. Comm. 972 (1978) and Synthesis, 934 (1978), by M. L. Roumestant et al., Tetrahedron, 33, 1283 (1977), and by A. Doutheau et al., Tetrahedron, 36, 1953 (1980), that the yield and the stereoselectivity are increased by carrying out the reaction in an aprotic polar solvent, such as N-methylpyrrolidone or diglyme, under reflux. Furthermore, D. A. Evans and A. M. Golob, J. Amer. Chem. Soc. 97, 4765 (1975), have shown that potassium alcoholates rearrange more easily than the alcohols themselves. Thus, certain alcohols of general formula (II), treated with potassium hydride in tetrahydrofuran under reflux, lead to the corresponding δ-ethylenic carbonyl products. However, these conditions are not suitable for the rearrangement of compounds having a low stability in a very basic medium.

It has now unexpectedly been found that the oxy-Cope rearrangement of a diethylenic alcohol of general formula (II) can be carried out at a temperature between −40° C. and the reflux temperature of the reaction mixture when it is effected in the presence of a catalytic amount of a divalent palladium complex, preferably in a suitable organic solvent; it is this finding which forms the subject of the present invention.

According to the present invention, the rearrangement of a diethylenic alcohol of general formula (II) to a carbonyl product of general formula (I) is advantageously carried out in the presence of a complex of divalent palladium chloride with benzonitrile, acetonitrile or cyclooctadiene, in an organic solvent, such as tetrahydrofuran, methylene chloride, benzene or diethyl ether, at a temperature of the order of 20° C., viz 10°-30° C. The rearrangement can also be carried out in the presence of divalent palladium chloride solubilised, for example, by lithium chloride in the form of the complex $PdCl_4Li_2$, optionally formed in situ.

In general, the catalyst is used in an amount of 0.01 to 0.15 mol per mol of diethylenic alcohol employed.

The δ-ethylenic ketone of general formula (I) can be isolated, optionally after washing the reaction mixture with water, by applying physical methods, such as distillation or chromatography.

The divalent palladium complex used as the catalyst can optionally be regenerated and used subsequently to carry out an oxy-Cope rearrangement.

The process according to the present invention makes it possible to obtain the δ-ethylenic ketones of general formula (I) in good yields, e.g. 70% and above, but the yields can vary according to the structure of the diethylenic alcohol used. Furthermore, the process is stereo-specific and generally leads to a preponderant proportion of one of the isomers.

The following non-limitative Examples illustrate the process of the present invention.

EXAMPLE 1

A mixture of 3,5-dimethylhexa-1,5-dien-3-ol (0.126 g; $10^{-3}$ mol) and dichloro-bis-(benzonitrile)-palladium(II) (0.0153 g; $0.04.10^{-3}$ mol) in tetrahydrofuran (7.5 cc) is kept at a temperature of the order of 20° C. under an inert atmosphere. After a reaction time of 5 hours, diethyl ether (50 cc) is added and the reaction mixture is then washed with water (7×10 cc). After drying of the organic layer over magnesium sulphate and evaporation of the solvent under reduced pressure (20 mm Hg; 2.7 kPa), 6-methylhept-6-en-2-one (0.125 g) is obtained, which has the following characteristics:

b.p.$_{101.3\ kPa}$=142°-144° C.

infra-red spectrum of a liquid film: characteristic bands at 3070, 1720, 1650 and 890 cm$^{-1}$.

NMR spectrum (CDCl$_3$, δ in ppm, J in Hz): 1.65 (s, 3H); 1.7 to 2.0 (m, 4H); 2.10 (s, 3H); 2.30 (t, J=7, 3H); 4.65 (s broadened, 2H).

The characteristics of this product are consistent with those which have been described by Viola et al., J. Amer. Chem. Soc., 89, 3462 (1967).

The yield is virtually quantitative.

EXAMPLE 2

By following the procedure of Example 1 but starting with 4-isopropenyl-3,7,11-trimethyldodeca-1,6,10-trien-3-ol (0.262 g; 10$^{-3}$ mol) and dichloro-bis-(benzonitrile)-palladium(II) (0.0575 g; 0.15.10$^{-3}$ mol), 6,10,14-trimethylpentadeca-6,9,13trien-2-one (0.223 g) is obtained, which has the following characteristics:

b.p.$_{0.0013\ kPa}$=123°-128° C.

infra-red spectrum of a liquid film: characteristic bands at 3030, 1715, 1670, 1445 and 1160 cm$^{-1}$.

NMR spectrum (CDCl$_3$, δ in ppm, J in Hz): 1.61 and 1.63 (2s broadened, 12H); 1.6 and 1.9 (m, 2H); 1.9 to 2.15 (m, 6H); 2.10 (s, 3H); 2.38 (t, J=7, 2H); 2.63 (t, J=7, 2H); 4.90 to 5.25 (m, 3H).

The spectral characteristics of this product are consistent with those described by Y. Fujita et al., Bull. Chem. Soc. Japan, 52, 1983 (1979).

EXAMPLE 3

A mixture of 3,5-dimethylhexa-1,5-dien-3-ol (0.126 g; 10$^{-3}$ mol) and dichloro-bis-(acetonitrile)palladium(II) (0.0108 g; 0.04.10$^{-3}$ mol) in tetrahydrofuran (7.5 cc) is kept at a temperature of the order of 25° C. under an inert atmosphere. After a reaction time of 2 hours 30 minutes, the tetrahydrofuran is removed under reduced pressure (30 mm Hg; 4 kPa). After filtration on a silica column using diethyl ether as the eluant, 6-methylhept-6-en-2-one (0.125 g) is obtained. The yield is virtually quantitative.

EXAMPLE 4

A mixture of 4-isopropenyl-3,7-dimethylocta-1,6-dien-3-ol (0.135 g; 7.10$^{-4}$ mol) and dichloro-bis-(benzonitrile)-palladium(II) (0.041 g) in tetrahydrofuran (5 cc) is kept at a temperature of the order of 20° C. After a reaction time of 2 hours 45 minutes, the reaction mixture is washed with softened water (12×5 cc). After drying over magnesium sulphate and evaporation of the solvent under reduced pressure (20 mm Hg; 2.7 kPa), 6,10-dimethylundeca-6,9-dien-2-one (0.103 g) is obtained in a yield of 76%.

It has the following characteristics:

infra-red spectrum of a liquid film: characteristic band at 1720 cm$^{-1}$.

NMR spectrum (CDCl$_3$, δ in ppm, J in Hz): 1.5 to 1.8 (b, 11H); 1.95 (t, 2H); 2.07 (s, 3H); 2.34 (t, J=7, 2H); 2.60 (dd, 2H); 4.8 to 5.3 (m, 2H).

EXAMPLE 5

A solution of 4-isopropenyl-3,7-dimethylocta-1,6-dien-3-ol (0.194 g; 10$^{-3}$ mol) and dichloro-bis-(benzonitrile)-palladium(II) (0.0358 g; 0.93.10$^{-4}$ mol) in benzene (1 cc) is stirred for 5 hours under an argon atmosphere and at a temperature of the order of 20° C. The reaction mixture is filtered on a column of silica gel (230-400 mesh), which has a height of 2 cm.

The eluate is concentrated and then distilled under reduced pressure. This yields a mixture (0.165 g) which contains, according to determination by vapour phase chromatography, 91% of 6,10-dimethylundeca-6,9-dien-2-one (b.p.$_{0.027\ kPa}$32 150° C.), the characteristics of which are identical to those of the product of Example 4.

The yield is 77%.

EXAMPLE 6

A solution of 4-isopropenyl-3,7-dimethylocta-1,6-dien-3-ol (0.194 g; 10$^{-3}$ mol), palladium(II) chloride (0.0232 g; 1.3.10$^{-4}$ mol) and lithium chloride (0.011 g; 2.6.10$^{-4}$ mol) in tetrahydrofuran (1 cc) is stirred for 25 hours under an argon atmosphere and at a temperature of the order of 20° C.

The reaction mixture is then treated in the same way and, under the conditions described in Example 5. This yields a mixture (0.170 g) which contains, according to determination by vapour phase chromatography, 80% of 6,10-dimethylundeca-6,9-dien-2-one and 5% of unconverted alcohol starting material.

The yield is 70%.

EXAMPLE 7

A solution of 4-isopropenyl-3,7-dimethylocta-1,6-dien-3-ol (0.194 g; 10$^{-3}$ mol) and dichloro-(cyclooctadienyl)-palladium(II) (0.0332 g; 1.6.10$^{-4}$ mol) in tetrahydrofuran (1 cc) is heated under reflux for 24 hours under an argon atmosphere.

The reaction mixture is then treated in the same way and under the conditions described in Example 5. This gives a virtually quantitative yield of a mixture which contains, according to determination by vapour phase chromatography, 70% of 6,10-dimethylundeca-6,9-dien-2-one and 19% of unconverted alcohol starting material.

EXAMPLE 8

A mixture of 2-isopropenyl-1-vinylcyclododecan-1-ol (0.100 g; 0.4.10$^{-3}$ mol) and dichloro-bis-(benzonitrile)-palladium(II) (0.007 g; 0.018.10$^{-3}$ mol) in tetrahydrofuran (5 cc) is kept at a temperature of the order of 20° C. under an inert atmosphere. After a reaction time of 6 hours, diethyl ether (75 cc) is added and the mixture is then washed with water (5×15 cc). After drying over magnesium sulphate, filtration and evaporation of the solvent under reduced pressure (20 mm Hg; 2.7 kPa), 5-methylcyclohexadec-5-en-1-one (0.065 g) is obtained, which has the following characteristics:

infra-red spectrum of a liquid film: characteristic band at 1715 cm$^{-1}$.

NMR spectrum (CDCl$_3$, δ in ppm): 4.95-5.22 (b, 14H); 2.2-2.5 (b, 4H); 1.9-2.2 (b, 4H); 1.2-1.9 (b, 21H).

EXAMPLE 9

A mixture of 2-isopropenyl-1-vinylcyclohexan-1-ol (0.166 g; 10$^{-3}$ mol) and dichloro-bis-(benzonitrile)-palladium(II) (0.038 g; 10$^{-4}$ mol) in tetrahydrofuran (5 cc) is kept at a temperature of the order of 20° C. under an inert atmosphere. After a reaction time of 24 hours, diethyl ether (75 cc) is added and the mixture is then washed with water (5×15 cc). After drying over magnesium sulphate, filtration and evaporation of the solvent under reduced pressure (20 mm Hg; 2.7 kPa), 5-methylcyclodec-5-en-1-one (0.070 g) is obtained, which has the following characteristics:

infra-red spectrum of a liquid film: characteristic bands at 1710 and 1100 cm$^{-1}$.

NMR spectrum (CDCl$_3$, δ in ppm): 1.47 (s, 3H), 1.55 to 2.15 (b, 10H); 2.15 to 2.37 (b, 2H); 2.37 to 2.62 (b, 2H); 5.2 (t, 1H, J=7 Hz).

EXAMPLE 10

A mixture of 2-isopropenyl-1-propenylcyclohexan-1-ol (0.090 g; 5.10$^{-4}$ mol) and dichloro-bis-(benzonitrile)-palladium(II) (0.008 g; 0.2.10$^{-4}$ mol) in tetrahydrofuran (5cc) is kept at a temperature of the order of 20° C. under an inert atmosphere. After a reaction time of 6 hours, diethyl ether (75 cc) is added and the mixture is then washed with water (5×15 cc). After drying with magnesium sulphate, filtration and evaporation of the solvent under reduced pressure (20 mm Hg; 2.7 kPa), alcohol starting material (0.050 g) is obtained together with 3,5-dimethylcyclodec-5-en-1-one (0.023 g), which has the following characteristics:

infra-red spectrum of a liquid film: characteristic bands at 1705 and 1100 cm$^{-1}$.

NMR spectrum (CDCl$_3$, δ in ppm): 0.97 (d, 3H, J=7 Hz); 1.5 (s, 3H); 1.07 to 2.7 (b, 13H); 5.2 (t, 1H, J=7 Hz).

We claim:

1. A process for the preparation of δ-ethylenic carbonyl compounds of the general formula:

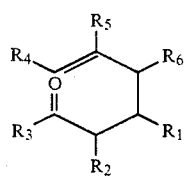

(I)

wherein R$_1$, R$_4$ and R$_6$ each represent a hydrogen atom or an acyclic radical containing 1 to 20 carbon atoms, the chain of which can contain one or more double or triple bonds, R$_2$ represents a hydrogen atom and R$_3$ and R$_5$ each represent an acyclic radical containing 1 to 20 carbon atoms, the chain of which can contain one or more double or triple bonds, or R$_3$ and R$_4$ together represent an alkylene radical (—CH$_2$—)$_n$ (wherein n represents an integer from 3 to 20 inclusive) in which one or more carbon atoms can optionally carry as substituent(s) one or more alkyl radicals containing 1 to 4 carbon atoms, by the rearrangement of a diethylenic alcohol of the general formula:

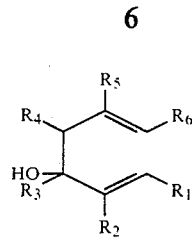

(II)

wherein R$_1$, R$_2$, R$_3$, R$_4$, R$_5$ and R$_6$ are as hereinbefore defined, which comprises carrying out the rearrangement at a temperature between −40° C. and the boiling point of the reaction mixture in the presence of a catalytic amount of a divalent palladium complex, and isolating the δ-ethylenic carbonyl product obtained.

2. A process according to claim 1 in which the divalent palladium complex is selected from dichloro-bis-(benzonitrile)-palladium(II), dichloro-bis-(acetonitrile)-palladium(II), dichloro-(cyclooctadienyl)-palladium-(II), and palladium(II) chloride in a soluble form.

3. A process according to claim 1 in which the reaction is carried out in an organic solvent.

4. A process according to claim 3 in which the reaction is carried out in tetrahydrofuran, methylene chloride, benzene or diethyl ether.

5. A process according to claim 2 in which the palladium chloride is solubilised by lithium chloride.

6. A process according to claim 3 in which the reaction is carried out at a temperature of from 10° to 30° C.

7. A process according to claim 1 in which the amount of palladium catalyst complex used is 0.01 to 0.15 mol per mol of diethylenic alcohol employed.

8. A process according to claim 1 in which a diethylenic alcohol of the general formula:

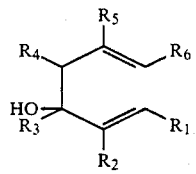

is used, wherein R$_1$, R$_4$ and R$_6$ each represent a hydrogen atom, an alkyl radical containing 1 to 20 carbon atoms, or an alkenyl or alkynyl radical containing 2 to 20 carbon atoms, R$_2$ represents a hydrogen atom and R$_3$ and R$_5$ each represent an alkyl radical containing 1 to 20 carbon atoms or an alkenyl or alkynyl radical containing 2 to 20 carbon atoms, or R$_3$ and R$_4$ together represent an alkylene radical (—CH$_2$—)$_n$ (wherein n is an integer from 3 to 20 inclusive) in which one or more carbon atoms can optionally carry as substituent(s) one or more alkyl radicals containing 1 to 4 carbon atoms, the said alkenyl and alkynyl radicals optionally having more than one double or triple bond.

* * * * *